United States Patent [19]

Dorgan et al.

[11] 4,389,406
[45] Jun. 21, 1983

[54] META-PYRAZOLYLAMINOTETRAMISOLE ANALOGS AND THEIR USE IN PHARMACEUTICAL COMPOSITIONS

[75] Inventors: Roderick J. Dorgan, Outwood; Richard A. Webster, Sutton, both of England

[73] Assignee: Beecham Group Limited, England

[21] Appl. No.: 263,927

[22] Filed: May 15, 1981

[30] Foreign Application Priority Data

May 30, 1980 [GB] United Kingdom ............... 8017694

[51] Int. Cl.³ .................. A61K 31/425; C07D 513/04
[52] U.S. Cl. .................................. 424/270; 548/154; 548/195
[58] Field of Search ....................... 424/270; 548/154

[56] References Cited

U.S. PATENT DOCUMENTS 3,673,205  6/1972  Spicer ................................. 424/270
4,137,321  1/1979  Leeming et al. ................... 548/154
4,143,147  3/1979  Leeming et al. ................... 548/154

FOREIGN PATENT DOCUMENTS 1365515  7/1974  United Kingdom .
1534411  5/1978  United Kingdom .
1516938  6/1978  United Kingdom .
1533347  8/1978  United Kingdom .

Primary Examiner—Nicholas S. Rizzo
Assistant Examiner—M. C. Eakin
Attorney, Agent, or Firm—Jacobs & Jacobs

[57] ABSTRACT

Compounds of formula (I) in the 1-form

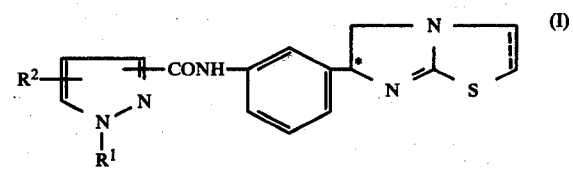

wherein $R^1$ and $R^2$ are the same or different and each is selected from hydrogen, optionally substituted ($C_{1-7}$) alkyl, optionally substituted aryl and aromatic heterocyclyl and the dotted line is an optional direct bond, and acid addition salts thereof, are useful in treating worm infections in mammals. Compounds (I) are produced by forming the amide of m-aminotetramisole or by closing the dihydroimidazoline ring.

11 Claims, No Drawings

META-PYRAZOLYLAMINOTETRAMISOLE ANALOGS AND THEIR USE IN PHARMACEUTICAL COMPOSITIONS

This invention relates to novel compounds having anthelmintic activity, to processes for their preparation and to pharmaceutical compositions containing them.

Tetramisole and levamisole are very well known anthelmintics of structure:

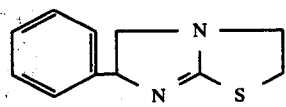

(A)

(tetramisole is the dl form, levamisole the l form).

Over the years since these anthelmintics first became known numerous publications have been made on analogues thereof. A study of these publications reveals that one class of active analogues are those of formula:

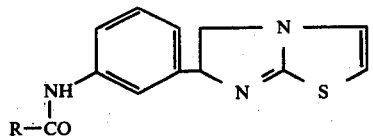

(B)

wherein the dotted line is an optionally present bond, and wherein R is for example alkyl (Belgian Pat. No. 764755), pyridyl (U.K. Pat. No. 1516938), isoxazolyl (Belgian Pat. No. 859949), isothiazolyl (Belgian Pat. No. 859950), and a whole range of substituents including alkyl, aromatic and heteroaromatic groups (Belgian Pat. No. 773062).

A group of compounds having anthelmintic activity has now been found which falls within the general scope of formula (B).

According to the present invention there is provided a compound of formula (I), or a salt thereof, in the l-form:

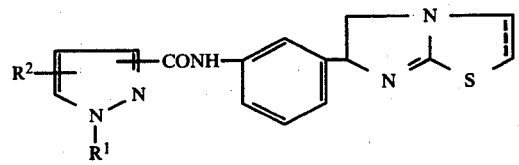

(I)

in which the dotted line is an optionally present double bond, $R^1$ and $R^2$ may be the same or different and each is hydrogen, an optionally substituted $C_1$ to $C_7$ alkyl group, an optionally substituted aryl group or a heterocyclic aromatic group.

Compounds of formula (I) also have activity against filarial worms

The compound of formula (I) may be optically pure or admixed in any proportion with the d-isomer, for instance, as the racemic or dl-form.

Preferably $R^1$ is a hydrogen atom, a methyl or optionally substituted phenyl group.

$R^2$ is preferably methyl and is conveniently located at the 3- or 5- position on the pyrazolyl ring.

Preferred compounds of formula (I) are those of formula (IA)

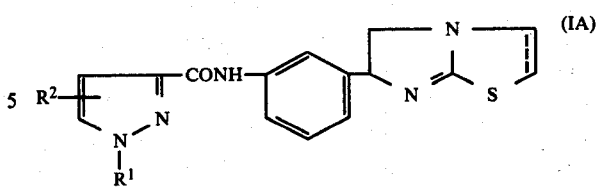

(IA)

Suitable salts of the compounds of formula (I) include the hydrochloride, hydrobromide, hydroiodide, nitrate, sulphate, acetate, lactate, and citrate salts.

According to a further aspect of the invention there is provided a process for the preparation of a compound of formula (I) in which the l- form of a compounnd of formula (V):

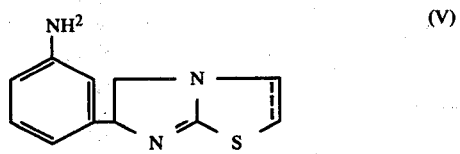

(V)

is reacted with an acid of formula (VI):

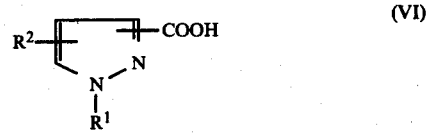

(VI)

or a "reactive derivative" thereof, in which $R^1$ and $R^2$ are as defined with respect to formula (I).

"Reactive derivative" when used herein means a derivative of the acid of formula (VI) which can be reacted with the amine of formula (V) to form an amido linkage between the acid group of the compound (VI) and the amino group of the amine.

Often this reactive derivative will be the acid halide, such as the acid chloride, of the acid (VI). Normally the reaction between an acid halide of (VI) and the amine (V) is conveniently carried out in an aqueous alcohol solvent, such as aqueous methanol. Alternatively the reaction can be carried out in an inert solvent, preferably in the presence of an acid acceptor. The inert solvent can be any solvent inert to both reactants, such as benzene, toluene or diethylether. The acid acceptor is suitably an organic base such as a tertiary amine e.g. triethylamine, trimethylamine, pyridine and picoline, or an inorganic acid acceptor, such as calcium carbonate, sodium carbonate, potassium carbonate and the like. It should also be noted that it is possible to use certain acid acceptors as the inert solvent, for example organic bases.

Another useful reactive derivative of the acid (VI) that may be used is an acid ester, such as a methyl, ethyl, propyl or butyl ester, in which case the reaction is normally carried out by heating the reactants together in an inert solvent such as dichloromethane, in the presence of a suitable condensing reagent such as a trialkylaluminium, especially trimethylaluminium.

The reaction may also be carried out by forming an anhydride of the acid (VI) in the usual manner, and reacting that with the amine—normally a conventional mixed anhydride will be used; or by reacting the acid (VI) and the amine in the presence of a dehydratingcatalyst such as a carbodiimide, for example dicyclohexylcarbodiimide.

The amines of formula (V), and the acids of formula (VI) may be prepared in known manner.

To prepare compounds of formula (I) in the dl-form, the corresponding dl-amine of formula (V) may simply be used. To prepare compounds of the formula (I) in the l-form, the corresponding l-form of the amine of formula (V) may simply be used.

Alternatively of course l-forms of compounds of the formula (I) may be prepared from their corresponding dl-form by resolution in conventional manner (as of course may l-forms of the amines of formula (V) be prepared from their corresponding dl-forms). Such resolution may be effected via an optically active salt formed from the racemic compound by reaction with an optionally active acid such as d-tartaric acid, or, preferably, d-or l-dibenzoyl tartaric acid. d-10-Camphor sulphonic acid is another optically active acid which may be used. Resolution reactions of this general nature are described in U.K. Pat. No. 1402689 and U.S. Pat. Nos. 3,463,786 and 3,673,205.

In a further aspect of the invention there is provided a process for the preparation of a compound of formula (I) in which the l- form of a compound of formula (VIII):

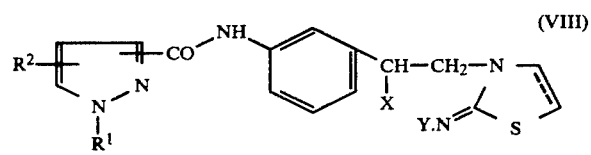

or a salt thereof, wherein $R^1$ and $R^2$ are as defined with respect to formula (I), X is chlorine or bromine, or hydroxyl, and Y is an imino protecting group, or a proton, is cyclised.

Suitably Y is a $C_{1-4}$ alkanoyl group, such as acetyl.

Suitably salts of the compound of formula (VIII) include the hydrochloride and hydrobromide.

The cyclisation reaction may be carried out in conventional manner, for example by heating the compound of formula (VIII) with excess of a base which does not hydrolyse the amide linkage, such as aqueous potassium carbonate, aqueous triethylamine, aqueous pyridine, or dilute ammonia solution. Suitably the reaction is carried out at 30° to 100° C. for a few hours. Conveniently chloroform is present in addition to the base, the chloroform layer being separated after reaction and evaporated to dryness to yield the desired product.

The compounds of formula (VIII) may be prepared by analogous processes, for example in general manner illustrated in U.K. Pat. No. 1516938.

Again if necessary resolution of either the product of this process, or of the compound of the formula (VIII) may be carried out in the manner hereinbefore described.

The salts of the compounds of the formula (I) may be prepared in entirely conventional manner, for example by reacting the compounds with the appropriate acid.

Compounds of formula (I) and (II) are useful in the treatment or prophylaxis of roundworm infections in animals, such as cattle, sheep and companion animals, and of filarial worm infections especially in companion animals.

Accordingly the invention also provides a pharmaceutical composition comprising a compound of the formula (I) or (II) or a pharmaceutically acceptable salt thereof, and a pharmaceutically acceptable carrier.

For oral administration the compositions may conveniently be in the form of aqueous solutions or suspensions of the active ingredient. Alternatively the active ingredient may be mixed in with an animal feedstuff or animal feed supplement.

Also the compound of formula (I) may be orally administered in the rumen devices described in Offenlegungsschrift No. 2824288 and U.K. Pat. Application No. 43555/78 (European Patent Application No. 79302445.6).

For parenteral administration the carrier will be any vehicle conveniently used for such administration, for example sterile water.

Alternatively the compound may be administered in a pour-on formulation using a conventional carrier such as dimethyl sulphoxide.

Suitably the compositions contain from 0.1 to 1000 mg/kg of animal body weight of active ingredient per dose, more suitably 1 to 50 mg/kg. For sustained release, devices as described above may contain from 1 to about 50 g, preferably about 3 g. The exact amount depending on the size of the animal and the period of drug release.

The invention also provides a method of treatment or prophylaxis of worm infections in animals, which comprises the administration to the sufferer of an effective amount of a compound of formula (I) or a pharmaceutically acceptable salt thereof.

It will be appreciated that it will normally be advisable to repeat the dosing of the infected animal with the compound of formula (I) according to conventional dosage regimes normally used with anthelmintics such as tetramisole and levamisole.

The following Examples illustrate the invention:

EXAMPLE 1

6-[m-(1,5-Dimethylpyrazole-3-carboxamido)phenyl]-2,3,5,6-tetrahydroimidazo[2,1-b]thiazole To 6-(m-aminophenyl)-2,3,5,6-tetrahydroimidazo-[2,1-b[thiazole (2.2 g, 10 mmol) in dry dichloromethane (30 ml) under nitrogen at room temperature was added trimethylaluminium (6 ml; 25% in hexane). After 20 mins 1,5-dimethylpyrazole-3-carboxylic acid ethyl ester (1.8 g; 11 mmol) in dry dichloromethane (2 ml) was added and the solution heated under reflux for 24 hours. Hydrochloric acid (20 ml; 2 N aqueous) was added slowly, the resulting solution basified with aqueous ammonia solution (100 ml; 5 N) and extracted with chloroform (3×200 ml). After drying (MgSO₄) the combined organic phases were concentrated in vacuo to afford an oil which was separated on aluminia eluting with chloroform to afford the amide (2.9 g; 85%). Treatment of the amide with isopropanolic hydrogen chloride gave a white solid after removal of the solvent. Recrystallisation from ethanol afforded the hydrochloride (2 g).

(Found: C: 53.17; H: 5.25; N: 18.15; Cl: 10.27. $C_{17}H_{19}N_5OS.1.1HCl$ requires C: 53.53; H: 5.27; N: 18.36; Cl: 10.23%) m.pt. 168°-170° C.

EXAMPLE 2

6-[m-(1,3-Dimethylpyrazole-5-carboxamido)phenyl]-2,3,5,6-tetrahydroimidazo[2,1-b]thiazole

To 6-(m-aminophenyl)-2,3,5,6-tetrahydroimidazo[2,1-b]thiazole (2.4 g, 11 mmol) in dry dichloromethane (30 ml) under nitrogen was added trimethylaluminium (4.8 ml; 25% in hexane). After 20 mins at room temperature 1,3-dimethylpyrazole-5-carboxylic acid ethyl ester (1.8 g, 11 mmol) in dry dichloromethane (1 ml) was added and the mixture heated under reflux for 24 hours. Hydrochloric acid (20 ml; 2 N aqueous) was added slowly, the resulting mixture basified with aqueous ammonia solution (5 N; 100 ml) and extracted with chloroform (3×200 ml) which after drying (MgSO$_4$) and concentrating in vacuo afforded an oil. Separation of the oil on alumina eluting with chloroform gave the amide (1.28 g; 34%).

(Found C: 59.55; H: 5.57; N: 20.53; S: 9.32. C$_{17}$H$_{19}$N$_5$OS requires C: 59.82; H: 5.57; N: 20.53; S: 9.38%) m.pt. 163°–4° C., which was converted to its hydrochloride salt with isopropanolic hydrogen chloride. Recrystallisation from methanol afforded the pure hydrochloride (1.4 g). (Found C: 47.97; H: 5.36; N: 15.97; Cl: 15.74; C$_{17}$H$_{20}$N$_5$OSCl.H$_2$O requires C: 47.22; H: 5.32; N: 16.20; Cl: 16.43%) m.pt. 150°–1° C.

EXAMPLE 3

6-[m-(3-Methyl-1-phenylpyrazole-5-carboxamido)-phenyl]-2,3,5,6-tetrahydroimidazo[2,1-b]thiazole

To 6-(m-aminophenyl)-2,3,5,6-tetrahydroimidazo[2,1-b]thiazole (1.43 g; 6.5 mmol) in dry dichloromethane (30 ml) under nitrogen at room temperature was added trimethylaluminium (10 ml; 25% in hexane). After 30 mins 3-methyl-1-phenylpyrazole 5-carboxylic acid ethyl ester (1.5 g, 6.5 mmol) in dry dichloromethane (5 ml) was added and the mixture heated under reflux for 24 hr. The reaction was quenched by the slow addition of hydrochloric acid (20 ml; 2 N aqueous), the resulting two phase system basified with aqueous ammonia solution (5 N) and extracted with chloroform (3×200 ml). After drying (MgSO$_4$) the combined organic phases were concentrated in vacuo to afford an oil which was separated by column chromatography on alumina eluting with chloroform. The major band was further purified by column chromatography on silica gel (60–120 mesh) eluting with chloroform to afford the amide (1.93 g; 62%) which was converted into its hydrochloride salt by the addition of isopropanolic hydrogen chloride. Recrystallisation from ethanol afforded the pure salt (0.7 g).

(Found C: 58.92; H: 4.96; N: 14.85; Cl: 7.91. C$_{22}$H$_{22}$N$_5$OSCl.½H$_2$O requires C: 58.86; H: 5.12; N: 15.60; Cl: 7.92%) m.pt. 164°–6° C.

EXAMPLE 4

6-[m-(5-Methyl-1-phenylpyrazole-3-carboxamido)-phenyl]-2,3,5,6-tetrahydroimidazo[2,1-b]thiazole

To 6-(m-aminophenyl)-2,3,5,6-tetrahydroimidazo[2,1-b]thiazole (1.9 g, 8.7 mmol) in dry dichloromethane (40 ml) under nitrogen at room temperature was added trimethylaluminium (6 ml: 25% in hexane). After 20 min 5-methyl-1-phenylpyrazole 3-carboxylic acid ethyl ester (2 g, 8.7 mmol) in dry dichloromethane (5 ml) was added and the mixture heated under reflux for 3 days. The reaction was quenched by the slow addition of hydrochloric acid (20 ml, 2 N aqueous), basified with aqueous ammonia solution (5 N) and extracted with chloroform (3×200 ml). After drying the organic phase was concentrated in vacuo to afford an oil which was separated by column chromatography on alumina eluting with chloroform to afford the amide (2.41 g; 69%). Addition of isopropanolic hydrogen chloride gave the hydrochloride salt (1.56 g) recrystallised from ethanol.

(Found C: 57.73; H: 5.23; H: 14.97; Cl: 7.79. C$_{22}$H$_{22}$N$_5$OSCl.H$_2$O requires C: 57.70; H: 5.25; N: 15.30; Cl: 7.76%) m.pt. 132°–4° C.

EXAMPLE 5

6-[m-(5-Methyl-1H-pyrazole-3-carboxamido)-phenyl]2,3,5,6-tetrahydroimidazo[2,1-b]thiazole

The title compound was prepared from 6-(m-aminophenyl)2,3,5,6-tetrahydroimidazo[2,1-b]thiazole and ethyl 5-methylpyrazole-3-carboxylate by the method outlined in Example 4. Treatment with isopropanolic HCl gave the dihydrochloride, m.p. 254°–5°.

Found C: 48.82; H: 4.60; N: 17.38; S: 7.67. C$_{16}$H$_{19}$N$_5$SOCl$_2$ requires C: 48.00; H: 4.78; N: 17.49; S: 8.01.

EXAMPLE 6

6-[m-(Pyrazole-3-carboxamido)phenyl]-2,3,5,6-tetrahydroimidazo[2,1-b]-thiazole

6-[m-(Pyrazole-3-carboxamido)phenyl]-2,3,5,6-tetrahydroimidazo[2,1-b]-thiazole was prepared by the method of Example 4. Treatment with isopropanolic hydrochloric acid gave the hydrochloride, m.p. 137°–9°.

Pharmacological Data Section

The oral activity of the compounds of Examples 1 to 5 against experimental infections of *Nematospiroides dubius* in the mouse were found. The activity was calculated from a comparison of the worm numbers of treated and control (untreated) animals.

| COMPOUND OF EXAMPLE NO. | SALT | DOSE mg/kg | ACTIVITY % |
| --- | --- | --- | --- |
| Ex. 1 | 1.1HCl | 50 | 99 |
|  |  | 5 | 40 |
| Ex. 2 | 2HCl | 50 | 83 |
|  |  | 5 | 0 |
| Ex. 3 | 1HCl | 50 | 27 |
|  |  | 5 | 0 |
| Ex. 4 | 1HCl | 50 | 98 |
|  |  | 5 | 26 |
| Ex. 5 | 2HCl | 50 | 100 |
|  |  | 25 | 100 |
|  |  | 10 | 82 |
|  |  | 5 | 56 |
|  |  | 1 | 23 |

A single oral dose of 5 mg/kg of the compound of Example 1, in the sheep, removed 70–100% of all important sheep roundworms.

We claim:

1. A compound of formula (I) in the l-form

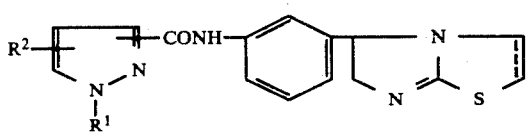 (I)

wherein R¹ and R² are the same or different and each is selected from hydrogen, (C₁₋₇) alkyl, and phenyl and the dotted line is an optional direct bond, or a pharmaceutically acceptable salt thereof.

2. A compound according to claim 1 wherein R¹ is hydrogen, methyl or phenyl.

3. A compound according to claim 1 wherein R² is methyl.

4. A compound according to claim 1 having the formula (IA):

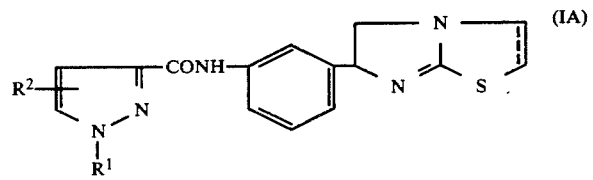 (IA)

wherein R¹ and R² have the same meanings as in claim 1.

5. A pharmaceutical composition having anthelmintic activity comprising a therapeutically effective amount of a compound of formula (I), or a pharmaceutically acceptable salt thereof, as defined in claim 1 and a pharmaceutically acceptable carrier therefor.

6. A composition according to claim 5 wherein the carrier is water.

7. A composition according to claim 5 wherein the carrier is an animal feedstuff or animal feed supplement.

8. A method for treating worm infections in mammals, said method comprising administering a therapeutically effective, non-toxic amount of a compound of formula (I), or a pharmaceutically acceptable salt thereof, as defined in claim 1 to a mammal infected with worms.

9. A method according to claim 8 wherein said compound is administered at from about 0.1 to about 1000 mg/kg of animal bodyweight.

10. A method of treating worm infections in mammals, which comprises administering a therapeutically effective, non-toxic amount of a a pharmaceutical composition according to claim 5 to a mammal infected with worms.

11. The compound according to claim 1, which is 6-[m-(1,5-dimethylpyrazole-3-carboxamido)phenyl]-2,3,5,6-tetrahydroimidazo[2,1-b]thiazole.

* * * * *

UNITED STATES PATENT AND TRADEMARK OFFICE
CERTIFICATE OF CORRECTION

PATENT NO. : 4,389,406
DATED : June 21, 1983
INVENTOR(S) : RODERICK JOHN DORGAN ETAL.

It is certified that error appears in the above-identified patent and that said Letters Patent are hereby corrected as shown below:

Column 7, line 5, delete the structural formula and insert

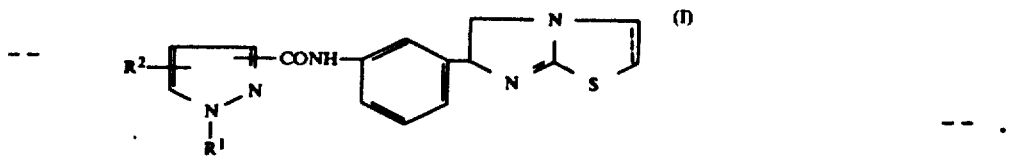

Signed and Sealed this

Twenty-fourth Day of January 1984

[SEAL]

Attest:

GERALD J. MOSSINGHOFF

Attesting Officer

Commissioner of Patents and Trademarks